United States Patent [19]

Frazer

[11] 4,130,112
[45] Dec. 19, 1978

[54] COUPLING APPARATUS FOR ULTRASONIC MEDICAL DIAGNOSTIC SYSTEM

[75] Inventor: Robert E. Frazer, La Canada, Calif.

[73] Assignee: The United States of America as represented by the Administrator of the National Aeronautics and Space Administration, Washington, D.C.

[21] Appl. No.: 741,749

[22] Filed: Nov. 15, 1976

[51] Int. Cl.² ............................................. A61B 10/00
[52] U.S. Cl. ...................................... 128/2 V; 73/633; 73/644
[58] Field of Search .............. 128/2 V, 2.05 Z, 24 A; 73/67.5 R, 67.6, 633, 644, 71.5 US

[56] References Cited

U.S. PATENT DOCUMENTS

| | | | |
|---|---|---|---|
| 2,752,914 | 7/1956 | Pohlman | 128/24 A |
| 3,480,002 | 11/1969 | Flaherty et al. | 128/2 V |
| 3,552,382 | 1/1971 | Mount | 128/2.05 Z |
| 3,603,303 | 9/1971 | Stouffer | 128/2 V |
| 3,765,403 | 10/1973 | Brenden | 128/2 V |
| 3,830,223 | 8/1974 | Beretsky et al. | 128/2 V |
| 3,964,296 | 6/1976 | Matzuk | 128/2 V X |

*Primary Examiner*—Lee S. Cohen
*Attorney, Agent, or Firm*—Monte F. Mott; John R. Manning; Wilfred Grifka

[57] ABSTRACT

Apparatus for the ultrasonic scanning of a breast or other tissue, including a cavity for receiving the breast, a vacuum for drawing the breast into intimate contact with the walls of the cavity, and transducers coupled through a fluid to the cavity to transmit sound waves through the breast. Each transducer lies at the end of a tapered chamber which has flexible walls and which is filled with fluid, so that the transducer can be moved in a raster pattern while the chamber walls flex accordingly, with sound transmission always occurring through the fluid.

8 Claims, 4 Drawing Figures

FIG. 1.

COUPLING APPARATUS FOR ULTRASONIC MEDICAL DIAGNOSTIC SYSTEM

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; U. S. C. 2457).

BACKGROUND OF THE INVENTION

This invention relates to ultrasonic scanning apparatus.

The diagnosis of living organs, such as the examination of the breasts for cancer, can be accomplished by passing ultrasonic waves through the organ, either in transmission or by reflection. The scanning of the entire area of the organ can be accomplished by moving the transducers in a raster to cover all regions thereof. Inasmuch as subtle changes in tissue density must be detected, it is important that there be uniform transmission paths between the transducers and the organ at all positions of the scanning transducers, so that only the non-uniformities in the tissue cause changes in the detected signal.

One method which can be used to scan a breast or other organ, involves the immersion of the organ and of the transducers in a common pool of water. The water transmits the ultrasonic waves with minimal loss and distortion. A system utilizing such immersion techniques is described in U.S. Patent Application Ser. No. 679,732, filed Apr. 23, 1976. Such direct immersion has several disadvantages. Where the breast of a patient is to be scanned by placing the patient prone over a water tank with the breast immersed, it is difficult to immerse the base or pectoral portion of the breast while keeping the head of the patient out of the water. Also, the breast is unrestrained and therefore the image can be blurred if there is any movement. Furthermore, the need to have the patient lie prone and immersed in water is somwhat uncomfortable and precautions must be taken to prevent contamination of the water.

SUMMARY OF THE INVENTION

In accordance with one embodiment of the present invention, an ultrasonic diagnostic system is provided which facilitates the coupling of ultrasonic transducers to tissue to be scanned. The system includes a cavity for receiving a breast or other tissue to be scanned and a vacuum for drawing the tissue into intimate contact with the walls of the cavity. The other side of the cavity walls opposite the tissue, contacts a fluid to which the ultrasonic transducers are coupled. Thus, where a breast is to be scanned, the patient does not have to lie prone with her breast in a pool of water, and scanning of the pectoral portion of the breast can be accomplished with a minimum of discomfort.

The coupling of the ultrasonic transducers to the tissue which lies in the cavity, in a manner that permits scanning movement of the transducer, such as in a raster pattern, can be easily accomplished by utilizing a tapered flexible body between each transducer and the outside walls of the cavity. The tapered flexible body comprises elastic walls forming a tapered chamber and a quantity of fluid filling the chamber, so that good sound wave coupling is established, while the transducers can be easily moved in a scanning pattern, all in a relatively compact and easily manipulated mechanism.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
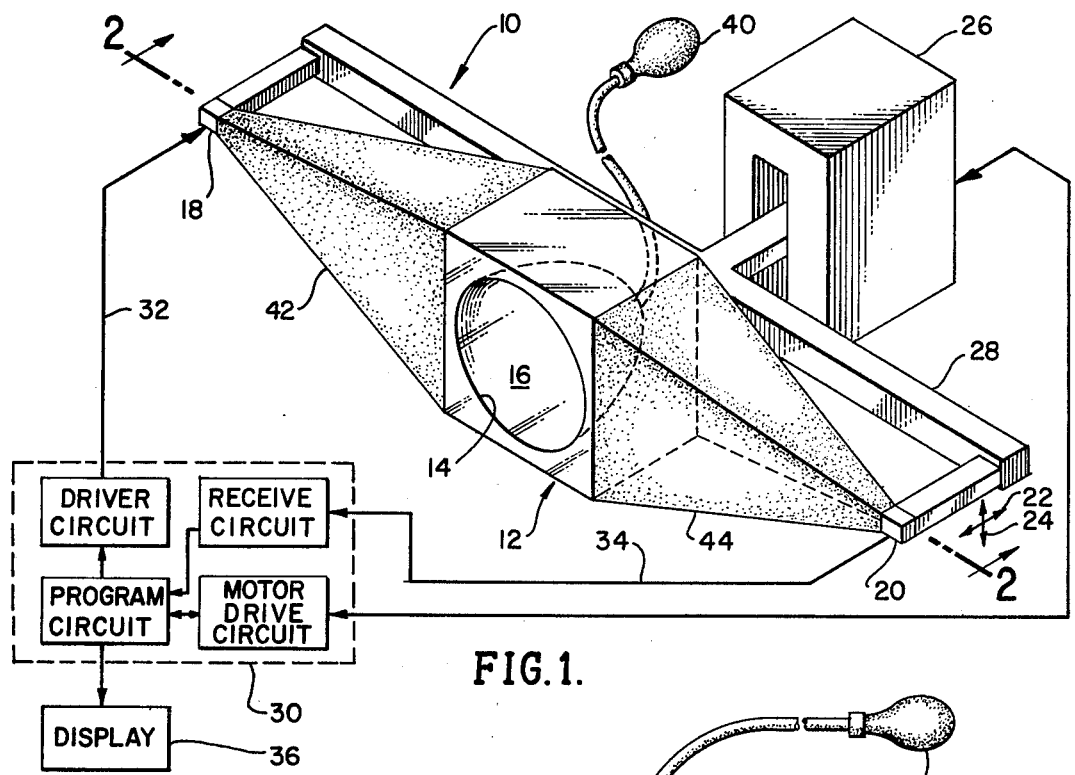
FIG. 1 is a perspective view of an ultrasonic diagnostic system constructed in accordance with one embodiment of the present invention.

FIG. 1 illustrates an ultrasound mammography diagnostic system 10 which includes a specimen-holding housing 12, the housing having walls 14 forming a cavity 16 which can receive the breast of a patient. An ultrasonic transmitting transducer 18 and an ultrasonic receiving transducer 20 lie on opposite sides of the cavity 16, so that sound waves can be transmitted through a patient's breast which is drawn into the cavity to enable diagnosis thereof, especially to find regions of slightly greater than normal density which might be cancerous. The ultrasonic transmitter transducer 18 and receiver transducer 20 may be utilized to transmit and then detect only sound waves which pass in substantially a straight line between them, and scanning of the entire breast is accomplished by moving both the transmitter and receiver simultaneously in a raster pattern, as indicated by arrows 22 and 24. A motor apparatus 26 is shown connected by a linkage 28 to both the transmitter 18 and the receiver 20, to move them in the desired raster pattern, while ultrasonic waves are transmitted and received. A circuit assembly 30 provides signals over lines 32 and 34 to the transmitter 18 and motor 26, and receives signals from the ultrasonic receiver 20, to operate the device. A display 36 coupled to the circuit assembly, can produce a display indicating the density of different regions of the patient's breast.

In order to enable accurate detection of sound waves passing directly through the tissue, it is necessary that the speed of sound waves be substantially predictable, and that there be a minimum of discontinuities that would either greatly attenuate the sound waves or that would unpredictably divert them. To minimize discontinuities, the tissue to be examined must be in intimate contact with the walls 14 of the cavity 16. To accomplish this, a vacuum pump 40 is provided, which is coupled to the cavity 16 to draw the breast into intimate contact with the cavity walls. The inside surface of the cavity and/or the outside of the breast may be coated with a liquid or gel to facilitate entry of the breast into the cavity and assure uniformly good coupling of the outside of the breast to the cavity walls.

Figure 2:
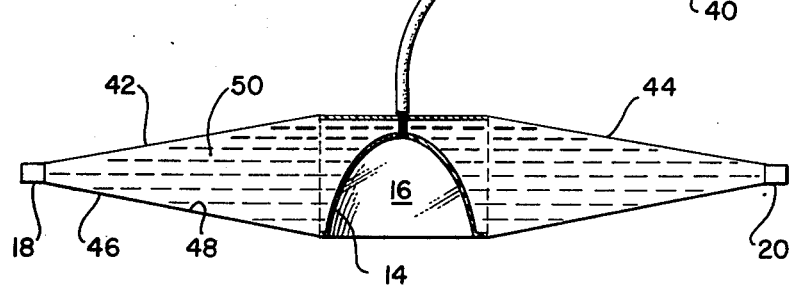
FIG. 2 is a view taken on the line 2—2 of FIG. 1.

In order to efficiently couple the transmitter and receiver transducers 18, 20 to the cavity walls 14, a pair of coupling bodies 42, 44 are provided which extend between each transducer such as 18 to one side of the cavity 16. Each of the coupling bodies such as 42, includes flexible walls 46 (FIG. 2) of a material such as rubber, which form a chamber 48, and a sound transmitting medium 50 such as water in the chamber. The flexible walls 46 and the liquid medium 50 therewithin, facilitate movement of the transducer 18 in a raster-scanning pattern to transmit sound waves through the cavity 16 and towards the receiving transducer 20, while maintaining uniform sound transmission at all transducer positions. The other coupling body 44 is similarly constructed. Link 28 assures that both transducers 18, 20 are always facing each other at opposite sides of the cavity, so that imaginary lines that connect the transducers pass through known portions of the tissue, or specimen, in the cavity as the transducers scan.

The housing 12 and the cavity walls 14 can be constructed of a material such as a transparent acrylic plastic, to permit viewing of the tissue to assure proper disposal within the cavity. The cavity walls 14 should be of substantially constant thickness, so that even though they have a somewhat different index of refraction than the tissue in the cavity and of the transmission medium 50 in each coupling body 42, 44, there will be only a small and predictable displacement of sound waves by the walls of the cavity. Water can be utilized as the sound-conducting medium 50, inasmuch as it has a sonic index of refraction very close to that of most living tissue, so that there is minimal displacement of sound along the path from one transducer 18 to the other 20. A solid rubber body could be utilized instead of a fluid-filled body, although ordinary rubber has a large attenuation. An easily deformed flexible solid material could be used if it had a low attenuation.

The coupling apparatus of this invention has several advantages over previous ultrasonic diagnostic systems wherein the tissue to be diagnosed was immersed in a water bath and the transducers were also immersed in the same water bath on opposite sides of the tissue. The rigid cavity walls 14 of the present invention enable a patient to remain upright, instead of requiring her to lie in a prone position. The rigid cavity walls 16 restrain the tissue from movement during a test, and facilitate cleaning by eliminating the possibility of contamination of water in a tank into which tissue is directly immersed. It also may be noted that the base pectoral portion of the breast is difficult to immerse in a water tank while the patient's head remains out of water, but the rigid cavity walls 14 allow reception of substantially the entire breast. In the most common diagnosis, transmitter and receiver transducers are positioned on opposite sides of the tissue to be examined; however, reflection methods can be utilized which can involve placing the transmitter and receiver (or a transducer that serves both functions) on the same side of the tissue-holding cavity. It also may be noted that while a tapered coupling body can produce minimal deformation of the coupling wall, it is also possible to utilize a non-tapered body with flexible walls to permit scanning movement of a transducer.

Figure 3:
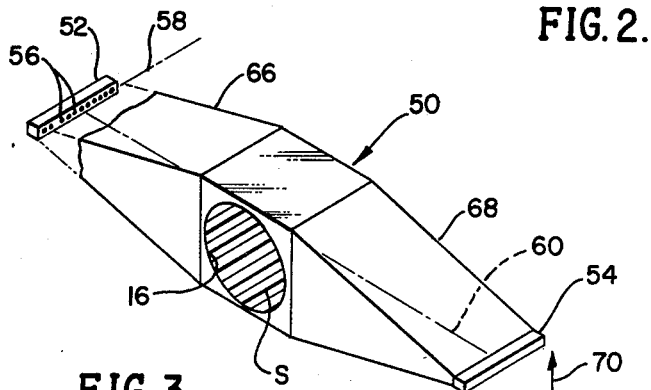
FIG. 3 is a partial perspective view of an ultrasonic diagnostic system constructed in accordance with another embodiment of the invention.
Figure 4:
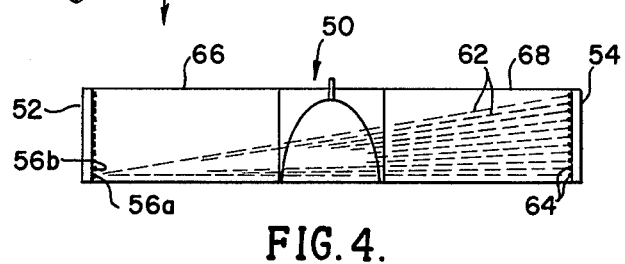
FIG. 4 is a sectional top view of the system of FIG. 3.

FIG. 3 illustrates a portion of a diagnosis sytem 50 which utilizes linear transducer arrays 52, 54 to scan a specimen S lying in a cavity 16. Each array such as the transmitting array 52, includes a plurality of individual transducers 56 arranged along a line 58 perpendicular to an imaginary line 60 which connects the centers of the two arrays 52, 54. The arrays are operated, as indicated in FIG. 4, with one transmitter transducer 56a at a time emitting sound, the emitted sound waves moving along numerous paths 62 to the receiving transducers 64 of the receiving array. A short time thereafter, a second transmitting transducer 56b is activated, and so forth. After each of the transducers 56 is activated in turn, both arrays 52, 54 may be shifted vertically so that sound passes through a different portion of the tissue being examined. Two coupling bodies 66, 68 are utilized which are similar to the coupling bodies 42, 44 except that the bodies 66, 68 have to be moved in only one direction of scanning, as indicated by arrows 70, and can be easily made with a taper only along their height rather than both along their height and width. The linear phased arrays operated in the manner described above, enable tomographic analysis to be performed rapidly. The apparatus of FIGS. 1 and 2 can be employed for tomographic analysis by not only scanning in the directions indicated by arrows 22 and 24, but by also using one of the transducers to scan while the other ramains stationary, although this would require a large amount of time if only a single transmitter and receiver are utilized.

Thus, the invention provides apparatus for assuring good sonic coupling between transducers and a tissue to be ultrasonically diagnosed, without requiring the tissue to be immersed in a fluid or to be directly contacted by the transducers. The apparatus also allows transducers to be moved in scanning patterns relative to the tissue being scanned, utilizing relatively compact and easily maintained equipment. This is accomplished by utilizing a cavity with solid walls for receiving the tissue, and by utilizing a vacuum to draw the tissue into intimate contact with the walls of the cavity. Of course, the solid cavity walls may be constructed of an elastic material such as rubber instead of a rigid material. Movement of the transducers, while maintaining them in good sonic coupling to the scanned tissue, without requiring immersion of the transducers in a large water bath, is accomplished by using flexible coupling bodies, such as a body constructed with flexible walls and filled with a liquid or gel.

Although particular embodiments of the invention have been described and illustrated herein, it is recognized that modifications and variations may readily occur to those skilled in the art and consequently it is intended that the claims be interpreted to cover such modifications and equivalents.

I claim:

1. An ultrasonic diagnostic system for examining a specimen comprising:
   a specimen-holding housing for receiving a specimen;
   an ultrasonic transmitter transducer;
   an ultrasonic receiver transducer;
   a flexible sound transmitting tapered body extending between a first side of said housing and a first of said transducers, with the small end of said tapered body nearest said first transducer;
   means for coupling a second of said transducers to said specimen-holding housing in operative relationship with respect to said first of said transducers; and
   means for moving said first transducer and said small end of said tapered body in a predetermined scanning pattern.

2. The system described in claim 1 wherein:
   said means for coupling comprises a second sound transmitting flexible tapered body extending between a second side of said housing which lies opposite said first side and said second transducer, with the small end of said tapered body nearest said second transducer.

3. The system described in claim 1 wherein;
said transmitter transducer comprises a linear array of transmitter elements;
said receiver transducer comprises a linear array of receiver elements; and
said moving means moves each of said linear arrays along a path perpendicular to the length of the array.

4. The system described in claim 1 wherein:
said tapered body includes walls of elastic material forming a tapered chamber, and fluid filling the chamber.

5. An ultrasonic mammography system comprising:
walls forming a substantially hemispheric cavity for receiving a breast to be examined, said walls being of substantially uniform thickness;
a pair of tapered sound-transmitting bodies lying on either side of said walls which form said cavity, with the large ends of said tapered bodies lying nearest said cavity and acoustically coupled thereto, each tapered body having elastic walls forming a tapered chamber and a quantity of fluid filling the chamber;
an ultrasonic transmitter and an ultrasonic receiver, each acoustically coupled to the small end of a different one of said tapered bodies; and
means for moving said transmitter and receiver in a scanning pattern.

6. An ultrasonic diagnostic system for examining a specimen comprising:
a specimen-engaging housing having walls for engaging the specimen; and
an ultrasonic scanner including transmitter means and receiver means positioned so that sound waves from said transmitter means pass through said walls and a specimen engaged therewith, to said receiver means; said ultrasonic scanner including a first sound transmitting flexible body extending between said housing and said transmitter means, a second sound transmitting flexible body extending between said housing and said receiver means, and transducer moving means for moving both said transmitter means and receiver means so that imaginary lines that connect them pass through different regions of a specimen engaged by said walls.

7. The system described in claim 6 wherein:
each of said bodies comprises flexible walls forming a chamber filled with a fluid.

8. The system described in claim 6 wherein:
each of said flexible bodies is tapered, with the smallest end of said first body nearest said transmitter means and the smallest end of said second body nearest said receiver means.

* * * * *